(12) United States Patent
Kisakibaru et al.

(10) Patent No.: US 10,508,261 B2
(45) Date of Patent: Dec. 17, 2019

(54) CULTURED ALGAE WATER CONCENTRATION SYSTEM, METHOD FOR OPERATING CULTURED ALGAE WATER CONCENTRATION SYSTEM, AND METHOD FOR CONCENTRATING ALGAE WATER CONTAINING CULTURED ALGAE

(71) Applicant: Kondoh Industries, Ltd., Tokyo (JP)

(72) Inventors: Toshiro Kisakibaru, Tokyo (JP); Motosuke Suzuki, Tokyo (JP)

(73) Assignee: Kondoh Industries, Ltd., Tokyo (JP)

( * ) Notice: Subject to any disclaimer, the term of this patent is extended or adjusted under 35 U.S.C. 154(b) by 25 days.

(21) Appl. No.: 15/512,667

(22) PCT Filed: Sep. 15, 2015

(86) PCT No.: PCT/JP2015/076146
§ 371 (c)(1),
(2) Date: Mar. 20, 2017

(87) PCT Pub. No.: WO2016/052174
PCT Pub. Date: Apr. 7, 2016

(65) Prior Publication Data
US 2017/0292107 A1    Oct. 12, 2017

(30) Foreign Application Priority Data
Feb. 27, 2015 (JP) .................. 2015-037507

(51) Int. Cl.
*C12N 1/12* (2006.01)
*C12N 1/02* (2006.01)
(Continued)

(52) U.S. Cl.
CPC .............. *C12N 1/12* (2013.01); *A01G 31/02* (2013.01); *A01G 33/00* (2013.01); *C12M 23/18* (2013.01);
(Continued)

(58) Field of Classification Search
None
See application file for complete search history.

(56) References Cited

U.S. PATENT DOCUMENTS 3,773,661 A * 11/1973 Talley ................ B01D 33/0376
210/388
5,659,977 A    8/1997 Jensen et al.

FOREIGN PATENT DOCUMENTS

JP    2009-118780 A    6/2009    .............. C12Q 1/06
JP    2014-076016 A    5/2014    .............. C12M 1/00
(Continued)

OTHER PUBLICATIONS

International Searching Authority, Japan Patent Office, International Search Report for International Application No. PCT/JP2015/076146, dated Nov. 2, 2015, 1 page.
(Continued)

*Primary Examiner* — Benjamin M Kurtz
(74) *Attorney, Agent, or Firm* — Sunstein Kann Murphy & Timbers LLP

(57) ABSTRACT

An object of the present invention is to provide: an algae water concentration system that efficiently concentrates algae water in a culture pond into algae water containing algae having a desired size, with a simple structure and at low cost; and a method for operating the same. A cultured algae water concentration system 100 comprises: an algae water supply unit 17 that has an algae water supply container 18 that stores algae water sent from the culture pond therein, and a supply container outlet port 19 through which the algae water is taken out from the algae water supply container; and an algae water concentration unit that has a concentration container 1 for receiving and concentrating the algae water from the algae water supply unit, a filter 3 which divides the concentration container into upper and lower spaces and does not pass algae having a predeter-
(Continued)

mined size or larger therethrough, a vibration device 5 that vibrates the filter in an out-of-plane direction, a concentration container algae water inlet port 7 which takes in the algae water to the concentration container and is arranged below the filter of the concentration container, a concentrated algae water outlet port 9 that is arranged below the filter of the concentration container and takes out algae water therethrough that has been concentrated in the concentration container, and a filtered water discharge port 8 that is arranged above the filter of the concentration container and discharges filtered water having passed through the filter.

9 Claims, 8 Drawing Sheets

(51) Int. Cl.
*C12M 1/00* (2006.01)
*C12M 1/34* (2006.01)
*C12M 1/26* (2006.01)
*A01G 33/00* (2006.01)
*A01G 31/02* (2006.01)

(52) U.S. Cl.
CPC ............ *C12M 33/08* (2013.01); *C12M 33/14* (2013.01); *C12M 41/00* (2013.01); *C12M 41/44* (2013.01); *C12M 47/02* (2013.01); *C12N 1/02* (2013.01)

(56) References Cited

FOREIGN PATENT DOCUMENTS

WO  WO 98/28407     7/1998  ............... C12N 1/06
WO  WO 2014/057889  *  4/2014

OTHER PUBLICATIONS

Website, "New Logic Research, Inc.—Technology Introduction", an internet page downloaded from the New Logic company website on Aug. 27, 2018, http://www.vsep.com/technology/index.htmi, 3 pages.

Ahmad, A.L., et al., "Comparison of Harvesting Methods for *Microalgae chlorella* sp. and its Potential use as a Biodiesel Feedstock," *Environmental Technology*, vol. 35, Issue 17, pp. 2244-2253, Sep.-Oct. 2014.

Ahmad, A.L., et al., "Crossflow Microfiltration of Microalgae Biomass for Biofuel Production," *Desalination*, vol. 302, pp. 65-70, Sep. 17, 2012.

European Patent Office, European Search Report, Application No. 15848036.8-1120, 10 pages, dated Mar. 8, 2018.

Nurra, C., et al., "Vibrating Membrane Filtration as Improved Technology for Microalgae Dewatering," *Bioresource Technology*, vol. 157, pp. 247-253, Apr. 2014.

Petruševski, B., et al., "Tangential Flow Filtration: A Method to Concentrate Freshwater Algae," *Water Research.*, vol. 29, Issue 5, pp. 1419-1429, May 1995.

Valdivia-Lefort, P., "An Optimal Harvesting and Dewatering System Mechanism for Microalgae," *Journal of Agricultural Machinery Science*, vol. 7, No. 2, pp. 211-215, 2011.

* cited by examiner

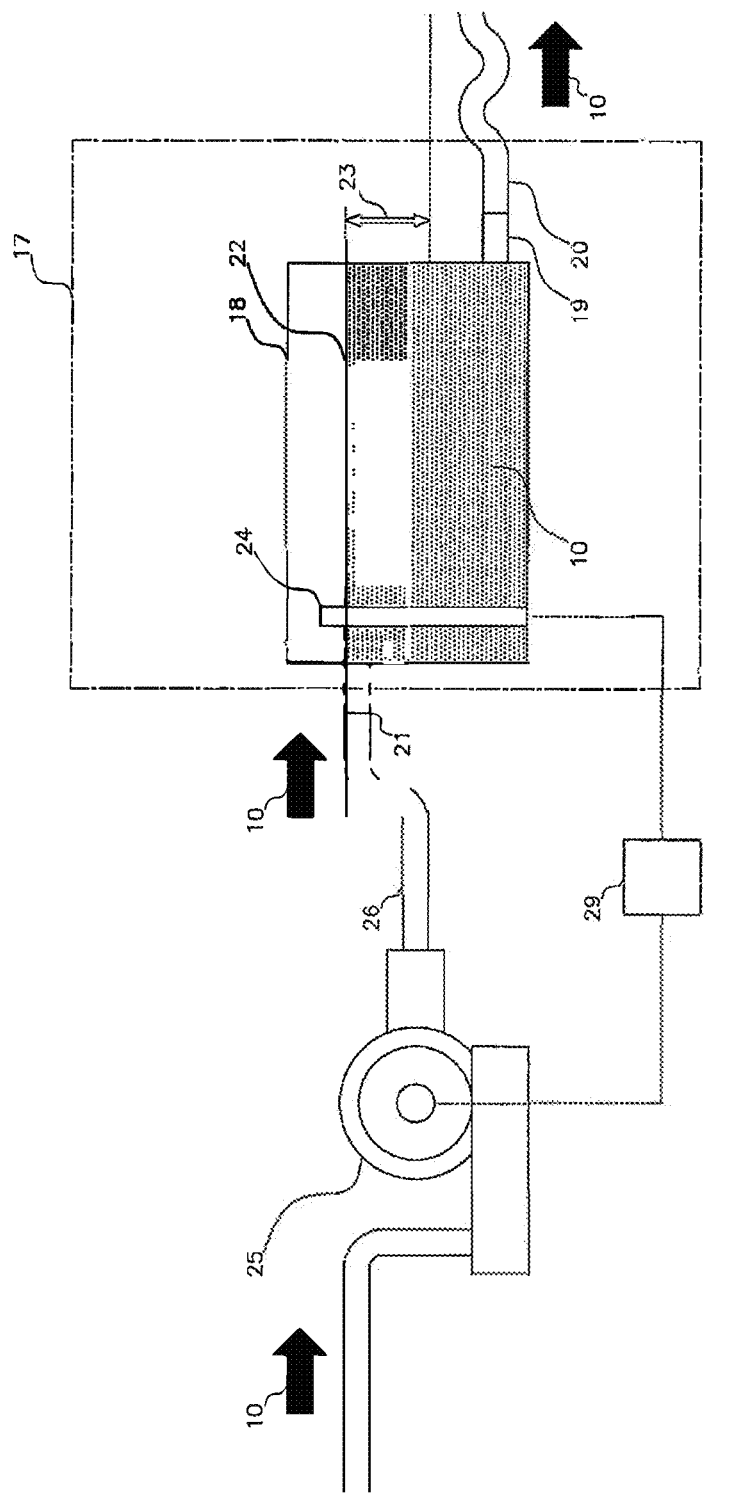

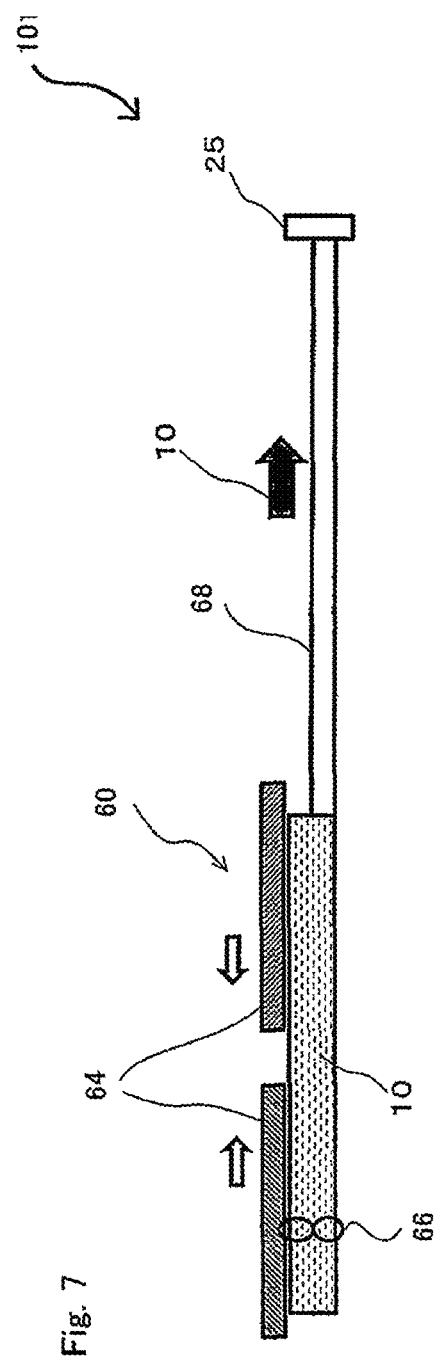

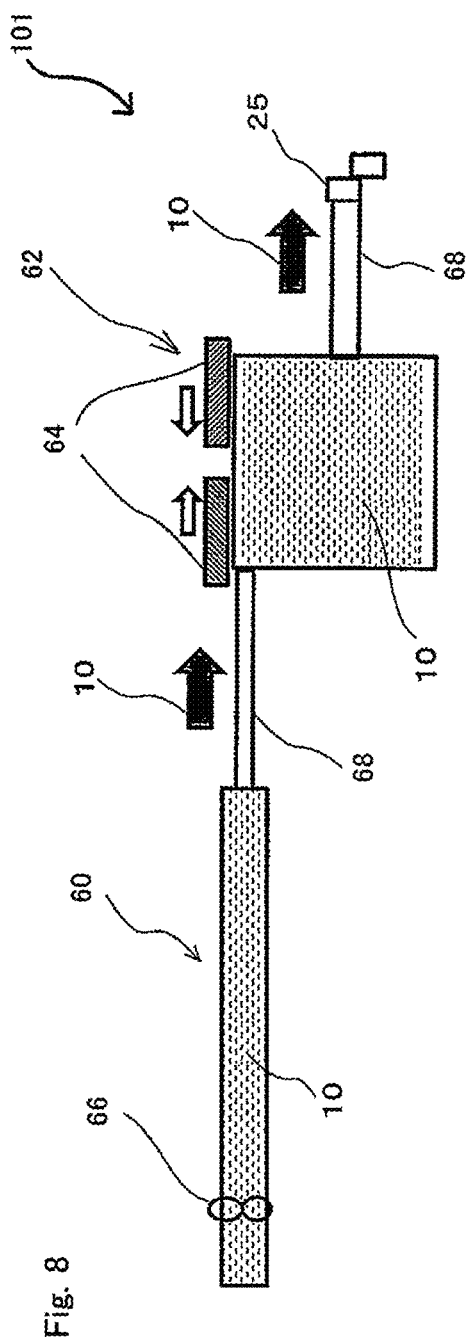

CULTURED ALGAE WATER CONCENTRATION SYSTEM, METHOD FOR OPERATING CULTURED ALGAE WATER CONCENTRATION SYSTEM, AND METHOD FOR CONCENTRATING ALGAE WATER CONTAINING CULTURED ALGAE

CROSS-REFERENCE TO RELATED APPLICATIONS

This application is a US national stage entry of PCT/JP2015/076146 filed Sep. 15, 2015, which itself claims priority to Japanese patent application 2014-204743 filed Oct. 3, 2014; Japanese patent application 2015-037507 2015 filed Feb. 27, 2015; and Japanese patent application 2015-066612 2015 filed Mar. 27, 2015, the entire contents of each of which is hereby incorporated by reference.

TECHNICAL FIELD

The present invention relates to an algae water concentration system for concentrating algae water containing algae, a method for operating the same, and a method for concentrating the algae water containing cultured algae.

BACKGROUND ART

In recent years, algae have received attention as a raw material for supplements such as EPA and DHA. In addition, there is a growing interest also in the algae as food. Furthermore, it is studied to use the algae as biofuel as alternative energy to fossil fuels. Thus, a demand for the algae is expected to increase, and the constructions of production plants for the algae are also proceeding both in Japan and abroad. From 2020, EU and other countries require to mix 20% of biofuel into a jet fuel. However, the jet fuel purified from cultured algae water has a problem of increased production costs if the jet fuel is produced by a current algae water concentration method, and the jet fuel is inferior to the fossil fuels in terms of the cost.

There are many types of algae, and there are also various sizes. Nannochloropsis is 5 µm and Botryococcus and Aurantiochytrium are approximately 50 µm. Thus, the size greatly varies depending on the type.

In the algae water plant, algae are cultured in a culture pond; and large-grown algae are collected, and are sent to the next step of drying and oil extraction. However, the algae which have been collected from the culture pond together with water contain algae having a size that does not satisfy the specification, and there is too much moisture for use in the drying and oil extraction step. Accordingly, it is necessary to concentrate the algae water while sorting the algae which have been cultured in the culture pond. Currently, it is a common practice to perform algae water concentration by a method of separating and concentrating the algae water with a centrifugal separator or a method of separating and concentrating the algae and the water with a flat membrane, a hollow fiber membrane or a reverse osmosis membrane. (See Patent Literature 1, for instance).

In the case of the separation and concentration method by the centrifugal separator, the amount of capital investment is large, and the facility maintenance cost and the operation cost increase. In addition, in the case of the separation and concentration method using the flat membrane, the hollow fiber membrane or the reverse osmosis membrane, it is necessary to apply high pressure to the separation and concentration. In addition, the membrane must be periodically cleaned (backwash) with high pressure water or gas, and high pressure equipment is needed such as a high pressure compressor. As a result, the amount of capital investment, the facility maintenance cost and the operation cost increase.

In addition, in the case of the above described hollow fiber membrane and the reverse osmosis membrane, the membranes may capture all the cultured algae having all the sizes because of the characteristics of the opening structure of the membranes; it becomes difficult to separate the algae of a size that does not satisfy the specification, and discharge the separated algae to a culture pond again to culture the algae; and there is a problem of reduced production efficiency of algae culture.

Furthermore, it is known that the algae secrete mucus (see Non Patent Literature 1, for instance). When the algae secrete mucus, there is a concern that the mucus gets entangled with a filter to cause clogging of the filter. Then, it is desirable to previously remove the mucus from the algae in the algae water which is concentrated by the algae water concentration system. The document concerning the mucus of the algae has not been found, but there is a detailed report concerning the mucus of coral (see Non Patent Literature 2, for instance).

It is said that the coral secretes the mucus for self-defense. The self-defense means the defense against the growth of organisms and bacteria which have adhered to the surface of the coral, the defense from ultraviolet rays, the defense from pollutants, the defense from drying at the time when the coral has been exposed to air at low tide, and the like. In addition, it is considered that the coral secretes the mucus also because of predation or in connection with photosynthesis of zooxanthellae that live symbiotically in the coral.

The present inventors have come to an idea that the present inventors can provide an algae water concentration system which prevents mucus from getting entangled with a filter to cause the clogging of the filter, by giving the algae an environment that the coral does not secrete the mucus, on the basis of an assumption that the algae secretes the mucus according to a similar reason to the coral.

PRIOR-ART PUBLICATION

Patent Literature

Patent Literature 1: Japanese Patent Laid-Open Publication No. 2014-76016

Non-Patent Literature

Non-Patent Literature 1: "Current Status of Algae at the Early 21st Century" edited by Terumitsu Hori, Masao Ohno, and Takeo Horiguchi, The Japanese Society of Phycology, in 2002, at Yamagata, p. 57 to 58

Non-Patent Literature 2: "The role of sand mucus in material circulation of coral reef ecological system" by Ryota Nakajima, and Yasuaki Tanaka, Journal of the Coral Reef Society of Japan, in 2014, Vol. 16 p. 3 to 27

Then, an object of the present invention is to provide: an algae water concentration system that efficiently concentrates algae water in a culture pond into algae water containing algae having a desired size, with a simple structure and at low cost; and a method for operating the same. Furthermore, another object of the present invention is to provide: a cultured algae water concentration system which can reduce an influence of mucus of algae, when concentrating algae water of a culture pond into algae water containing algae having a desired size by using a filter; a method for operating the cultured algae water concentration system; and a method for concentrating algae water containing cultured algae.

DISCLOSURE OF THE INVENTION

In order to solve the above described problems, as is shown in FIG. 1, for instance, a cultured algae water concentration system 100 according to the first aspect of the present invention comprises: an algae water supply unit 17 that receives algae water 10 containing cultured algae from a culture pond, stores the algae water therein, and has an algae water supply container 18 that stores the algae water 10 therein, a supply container inlet port 21 through which the algae water supply container 18 takes in the algae water 10, and a supply container outlet port 19 through which the algae water 10 is taken out from the algae water supply container 18; and an algae water concentration unit 16 that concentrates the algae water 10 which has been supplied from the algae water supply unit 17, and that has a concentration container 1 for receiving and concentrating the algae water 10, a filter 3 that divides the concentration container 1 into upper and lower spaces and does not pass algae having a predetermined size or larger therethrough, a vibration device 5 that vibrates the filter 3 in an out-of-plane direction, a concentration container algae water inlet port 7 that is in communication with a supply container outlet port 19, takes in the algae water 10 to the concentration container 1, and is arranged below the filter 3 of the concentration container 1, a concentrated algae water outlet port 9 that is arranged below the filter 3 of the concentration container 1 and takes out algae water 13 therethrough that has been concentrated in the concentration container 1, and a filtered water discharge port 8 that is arranged above the filter 3 of the concentration container 1 and discharges filtered water 12 having passed through the filter 3.

When the cultured algae water concentration system is thus configured, the algae water that has been sent from the culture pond and contains the cultured algae passes through the algae water supply container, and is guided to a space below the filter of the concentration container. In algae water that has reached the filter out of the algae water in the space below the filter of the concentration container, algae that are smaller than a predetermined size and water pass through the filter and are discharged from the filtered water discharge port. Algae that are larger than the predetermined size do not pass through the filter, and stay in the lower space. At this time, the filter vibrates in the out-of-plane direction due to the vibration device, and accordingly the large algae are reflected by the filter and do not adhere to the filter surface. Therefore, an apparatus for cleaning the filter surface is unnecessary. In this way, the cultured algae water concentration system is enabled to take out the algae water that has been concentrated by reducing the algae that are smaller than the predetermined size and the water, from the concentrated algae water outlet port. Accordingly, the system becomes an algae water concentration system that efficiently concentrates algae water of the culture pond into algae water containing algae having a desired size, with a simple structure and at low cost.

A cultured algae water concentration system according to a second aspect of the present invention is a cultured algae water concentration system 100 according to the first aspect, which further comprises a concentrated algae water flow rate adjustment apparatus 40 that adjusts an amount of concentrated algae water 13 flowing out through the concentrated algae water outlet port 9, as is shown in FIG. 1, for instance.

When the system is thus configured, the adjustment apparatus can adjust the amount of concentrated algae water that flows out from the concentrated algae water outlet port, with respect to the amount of the algae water which is sent from the culture pond, passes through the algae water supply container and is supplied to the concentration container. Therefore, the flow rate adjustment apparatus can prevent the amount of the algae water that flows out from the concentrated algae water outlet port from excessively increasing, and the water level of the algae water from descending below the filter in the concentration container. Furthermore, a function of adjusting the amount of the algae water that flows out from the concentrated algae water outlet port results in also serving as a function of adjusting the amount of the filtered water that is discharged from the filtered water discharge port, and the system can concentrate the algae water to a desired concentration.

The cultured algae water concentration system according to a third aspect of the present invention is, as shown in FIGS. 1 and 2, for instance, the cultured algae water concentration system 100 according to the first or second aspect, which further comprises: a liquid level meter 24 that measures the liquid level of the algae water 10 which is stored in the algae water supply container 18; and algae water flow rate adjustment devices 25 and 29 that adjust the flow rate of the algae water 10 to be sent to the algae water supply container 18 from the culture pond, based on the liquid level which has been measured by the liquid level meter 24. When the system is thus configured, the algae water flow rate adjustment devices can set a difference between heights of the liquid level of the algae water in the algae water supply container and the filter level of the concentration container (hereinafter referred to as "water level difference"), to a desired value. Specifically, the algae water flow rate adjustment devices can adjust a force with which the concentrated algae water pushes up the filter of the concentration container. Therefore, the flow rate adjustment devices can prevent the algae water from pushing up the filter with such a large force that the vibration device cannot vibrate the filter.

The cultured algae water concentration system according to a fourth aspect of the present invention is the cultured algae water concentration system 100 according to any one of the first to third aspects, wherein the filtered water discharge port 8 is arranged at a position higher than the highest position of the filter 3, which is vibrated by the vibration device 5, as is shown in FIG. 1, for instance. When the system is thus configured, the filter is not positioned above the liquid level of the concentrated algae water or filtered water. Therefore, the system can prevent the filter from being exposed to the air, the algae water remaining in the opening of the filter from obstructing the opening, and the filter from being unable to function.

The cultured algae water concentration system according to a fifth aspect of the present invention is the cultured algae water concentration system 100 according to any one of the first to fourth aspects, as is shown in FIGS. 5 and 6, for instance, wherein the filter 3 is held by a filter frame 4' that has an annular outer frame 4A and reinforcing plates 4B of which the sheet number is multiples of 3 and which extend from the center 4C to the annular outer frame 4A in a radial direction at equal central angles, wherein the reinforcing plates 4B have vibration devices 5A, 5B and 5C thereon, respectively, wherein the vibration devices 5A, 5B, 5C are connected to the reinforcing plates 4B of the filter frame 4' or intersections between the reinforcing plates 4B and the annular outer frame 4A, respectively, to vibrate the filter 3 through the filter frame 4', and wherein electric currents of an R phase, an S phase and a T phase of a three-phase alternating current are supplied to the vibration devices 5A, 5B and 5C in the order of the circumferential direction so that the vibration devices 5A, 5B and 5C vibrate out of phase. When the system is thus configured, since the filter vibrates while having a phase difference in the circumferential direction, a flow is generated in a direction parallel to the filter occurs in the algae water in the concentration container below the filter to prevent the clogging of the filter due to the algae.

The cultured algae water concentration system according to a sixth aspect of the present invention is, as is shown in FIG. 6, for instance, a cultured algae water concentration system 100 according to the fifth aspect, which further comprises a frequency converter 52 that converts the frequency of the three-phase alternating current. When the system is thus configured, since the frequency converter can change the speed at which the filter vibrates while having a phase difference in the circumferential direction, the flow speed of the flow can be changed in the direction parallel to the filter of the algae water below the filter in the concentration container.

A method for operating the cultured algae water concentration system, according to a seventh aspect of the present invention, is a method for operating the cultured algae water concentration system 100 according to any one of the first to sixth aspects, as is shown in FIG. 1, for instance. It activates the vibration device 5, and then supplies the algae water 10 from the algae water supply unit 17 to the algae water concentration unit 16. When the method is thus configured, since the algae water is supplied after the filter has been vibrated by the vibration device, and is filtered by the filter, the algae can be prevented from adhering to the filter.

In order to solve the above described problems, a method for concentrating algae water containing cultured algae according to an eighth aspect of the present invention comprises, as is shown in FIG. 1 and FIGS. 7 and 8, for instance: a step of storing algae water 10 containing cultured algae for a predetermined time period, in a state in which light is blocked, in which there is no water flow, and in which nutrients are not given; a step of introducing the stored algae water 10 into a lower space of a concentration container 1 that is divided into upper and lower spaces by a filter 3; a step of vibrating the filter 3 in an out-of-plane direction to filter the algae water 10 that has been introduced into the concentration container 1; and a step of separating algae water 11 that has passed through the filter 3 to collect algae water 13 containing algae that do not pass through the filter 3.

When the method is thus configured, since the algae water containing the cultured algae is stored for a predetermined time period, in a state in which light is blocked, in which there is no water flow, and in which nutrients are not given, even algae which are easy to secrete the mucus stop the secretion of the mucus so that algae having no mucus can be obtained. After that, the algae water is guided to the space below the filter of the concentration container. In the algae water that has reached the filter out of the algae water in the space below the filter of the concentration container, algae that are smaller than a predetermined size and the water pass through the filter to be discharged from a filtered water discharge port. Algae that are larger than the predetermined size do not pass through the filter to stay in the lower space. At this time, since the filter vibrates in the out-of-plane direction due to the vibration device, the large algae are reflected by the filter and do not adhere to the filter surface. Furthermore, since the mucus has been removed, the filter does not cause clogging by the mucus. Therefore, an apparatus for cleaning the filter surface is unnecessary. In this way, the cultured algae water concentration system is enabled to take out the algae water that has been concentrated by reducing the algae that are smaller than the predetermined size and the water, from the concentrated algae water outlet port. Accordingly, the method becomes a method that efficiently concentrates algae water of the culture pond into algae water containing algae having a desired size, with a simple structure and at low cost.

A method for concentrating algae water containing cultured algae according to a ninth aspect of the present invention is the method according to the eighth aspect, wherein the predetermined time period is in between 3 days and 5 days. When the method is thus configured, since the algae are stored for 3 to 5 days in a state in which light is blocked, in which there is no water flow, and in which nutrients are not given, the algae stop the secretion of the mucus to have almost completely no mucus.

A cultured algae water concentration system 101 according to a tenth aspect of the present invention comprises, as is shown in FIGS. 1 and 8, for instance: an algae water storage unit 62 that stores algae water 10 containing cultured algae therein, and stores the algae water 10 for a predetermined time period, in a state in which light is blocked, in which there is no water flow, and in which nutrients are not given; and an algae water concentration unit 16 that concentrates the algae water 10 which has been supplied from the algae water storage unit 62, and that has a concentration container 1 for receiving and concentrating the algae water 10, a filter 3 that divides the concentration container 1 into upper and lower spaces and does not pass algae having a predetermined size or larger therethrough, a vibration device 5 that vibrates the filter 3 in an out-of-plane direction, an algae water inlet port 7 that takes in the algae water 10 therethrough which has been stored in the concentration container 1, the algae water inlet port being arranged below the filter 3 of the concentration container 1, a concentrated algae water outlet port 9 that is arranged below the filter 3 of the concentration container 1 and takes out algae water 13 therethrough that has been concentrated in the concentration container 1, and a filtered water discharge port 8 that is arranged above the filter 3 of the concentration container 1 and discharges filtered water 12 having passed through the filter 3.

When the method is thus configured, since the algae water containing the cultured algae are stored in the algae water storage unit for a predetermined time period, in a state in which light is blocked, in which there is no water flow, and in which nutrients are not given, even algae which are easy to secrete the mucus stop the secretion of the mucus to have no mucus. After that, the algae water is guided to the space below the filter of the concentration container. In the algae water which has reached the filter out of the algae water in the space below the filter of the concentration container, algae having smaller than a predetermined size and the water pass through the filter, and are discharged from the filtered water discharge port. Algae that are larger than the predetermined size do not pass through the filter to stay in the lower space. At this time, since the filter vibrates in the out-of-plane direction due to the vibration device, the large algae are reflected by the filter and do not adhere to the filter surface. Furthermore, since the algae are in a state of having no mucus, the filter is not clogged by the mucus. Therefore, an apparatus for cleaning the filter surface is unnecessary. In this way, the cultured algae water concentration system is enabled to take out the algae water that has been concentrated by reducing the algae that are smaller than the predetermined size and the water, from the concentrated algae water outlet port. Accordingly, a system is provided that efficiently concentrates algae water of the culture pond into algae water containing algae having a desired size, with a simple structure and at low cost.

A cultured algae water concentration system according to an eleventh aspect of the present invention is the system 101 according to the tenth aspect, which further comprises a flow rate adjustment apparatus 40 that adjusts an amount of concentrated algae water 13 flowing out from the concentrated algae water outlet port 9, as is shown in FIG. 1, for instance. When the system is thus configured, the flow rate adjustment apparatus can adjust the amount of concentrated algae water that flows out from the concentrated algae water outlet port, with respect to the amount of the algae water which is sent from the culture pond through the algae water storage unit to the concentration container. Therefore, the flow rate adjustment apparatus can prevent the amount of the algae water that flows out from the concentrated algae water outlet port from excessively increasing, and the water level of the algae water from descending below the filter in the concentration container. Furthermore, since the amount of the algae water that flows out from the concentrated algae water outlet port is adjusted r the amount of the filtered water that is discharged from the filtered water discharge port is adjusted. Thus the system can concentrate the algae water to a desired concentration.

A cultured algae water concentration system according to a twelfth aspect of the present invention is the cultured algae water concentration system 101 according to the tenth or eleventh aspect, as is shown in FIG. 1, for instance, which further comprises: an algae water supply unit 17 that receives the algae water 10 stored in the algae water storage unit 62 and stores the algae water 10 therein. The algae water supply unit 17 has an algae water supply container 18 that stores the algae water 10 therein, a supply container inlet port 21 through which the algae water supply container 18 takes in the algae water 10, and a supply container outlet port 19 through which the algae water 10 is taken out from the algae water supply container 18. When the system is thus configured, the algae water that has been sent from the culture pond and contains the cultured algae passes through the algae water supply container, and is guided to a space below the filter of the concentration container. The system adjusts the liquid level of the algae water in the algae water supply container, and thereby can adjust a force with which the concentrated algae water pushes up the filter of the concentration container. Therefore, the system can prevent the algae water from pushing up the filter with such a large force that the vibration device cannot vibrate the filter.

A cultured algae water concentration system according to a thirteenth aspect of the present invention is the cultured algae water concentration system 101 according to the twelfth aspect, as is shown in FIGS. 1, 2, and 8, for instance, which further comprises: a liquid level meter 24 that measures the liquid level of the algae water 10 which is stored in the algae water supply container 18; and flow rate adjustment devices 25 and 29 that adjust the flow rate of the algae water 10 to be sent to the algae water supply container 18 from the algae water storage unit 62 based on the liquid level that has been measured by the liquid level meter 24. When the system is thus configured, since the flow rate adjustment devices can accurately adjust the liquid level of the algae water in the algae water supply container, the system can surely prevent the algae water from pushing up the filter with such a large force that the vibration device cannot vibrate the filter.

A cultured algae water concentration system according to a fourteenth aspect of the present invention is the cultured algae water concentration system 101 according to any one of the tenth to thirteenth aspects, wherein the filtered water discharge port 8 is arranged at a position higher than the highest position of the filter 3 that is vibrated by the vibration device 5, as is shown in FIG. 1, for instance. When the system is thus configured, the filter is not positioned above the liquid level of the concentrated algae water or filtered water. Therefore, the system can prevent the filter from being exposed to the air, the algae water remaining in the opening of the filter from obstructing the opening, and the filter from being unable to function.

A cultured algae water concentration system according to a fifteenth aspect of the present invention is the cultured algae water concentration system 101 according to any one of the tenth to fourteenth aspects, wherein the predetermined time period is between 3 days and 5 days. When the system is thus configured, since the algae are stored for 3 to 5 days in a state in which light is blocked, in which there is no water flow, and in which nutrients are not given, the algae stop the secretion of the mucus to have almost completely no mucus.

A cultured algae water concentration system according to a sixteenth aspect of the present invention is the cultured algae water concentration system 101 according to any one of the tenth to fifteenth aspects, wherein the algae water storage unit is the container 62 that stores the algae water 10 that has been received from the culture pond 60. When the system is thus configured, it is easy for the system to store the algae water in a state in which light is blocked, in which there is no water flow, and in which nutrients are not given, because the algae water storage unit is a container.

A cultured algae water concentration system according to a seventeenth aspect of the present invention is the cultured algae water concentration system 101 according to any one of the tenth to fifteenth aspects, wherein the algae water storage unit is a pond 62 that stores the algae water 10 that has been received from the culture pond 60, as is shown in FIG. 8, for instance. When the system is thus configured, it is possible to inexpensively prepare a large algae water storage unit, because the algae water storage unit is a pond.

A method for operating the cultured algae water concentration system according to an eighteenth aspect of the present invention comprises a step of operating the vibration device 5, and then a step of supplying the algae water 10 from the algae water storage unit 62 to the algae water concentration unit 16, in the cultured algae water concentration system 101 according to any one of the tenth to seventeenth aspects. When the method is thus configured, the algae water is supplied after the filter has been vibrated by the vibration device, and is filtered by the filter. Thus, the algae can be prevented from adhering to the filter.

The algae water concentration system of the present invention comprises: an algae water supply unit that receives algae water containing cultured algae from a culture pond, stores the algae water therein, and has an algae water supply container that stores the algae water therein, a supply container inlet port through which the algae water supply container takes in the algae water, and a supply container outlet port through which the algae water is taken out from the algae water supply container; and an algae water concentration unit that concentrates the algae water which has been supplied from the algae water supply unit, and that has a concentration container for receiving and concentrating the algae water, a filter that divides the concentration container into upper and lower spaces and does not pass algae having a predetermined size or larger therethrough, a vibration device that vibrates the filter in an out-of-plane direction, a concentration container algae water inlet port that is in communication with a supply container outlet port, takes in the algae water to the concentration container and is arranged below the filter of the concentration container, a concentrated algae water outlet port that is arranged below the filter of the concentration container and takes out algae water therethrough that has been concentrated in the concentration container, and a filtered water discharge port that is arranged above the filter of the concentration container and discharges filtered water having passed through the filter. Thus the system can efficiently concentrate algae water of the culture pond into algae water containing algae having a desired size, with a simple structure and at low cost.

The method for operating the algae water concentration system of the present invention comprises a step of operating the vibration device and then a step of supplying the algae water from the algae water supply unit to the algae water concentration unit. Thus the algae can be prevented from adhering to the filter.

According to the method for receiving and concentrating algae water that has been sent from the culture pond and contains the cultured algae in the present invention, the algae water that has been sent from the culture pond and contains the cultured algae is stored for a predetermined time period, in a state in which light is blocked, in which there is no water flow, and in which nutrients are not given. Thus the algae stop the secretion of mucus to have no mucus. After that, the algae water is subjected to filtering treatment in which the filter vibrates in the out-of-plane direction. Thus the algae do not adhere to the filter surface and the filter can be prevented from being clogged by the algae due to the mucus.

According to the algae water concentration system of the present invention, since the algae water that has been sent from the culture pond and contains the cultured algae is stored for a predetermined time period, in a state in which light is blocked, in which there is no water flow, and in which nutrients are not given in the algae water storage unit, the algae stop the secretion of the mucus to have no mucus. After that, the algae water is guided to the space below the filter of the concentration container, and is concentrated by the filter that vibrates in the out-of-plane direction. Therefore, the algae do not adhere to the filter surface and the filter can be prevented from being clogged by the algae due to the mucus.

The basic Japanese patent applications, No. 2014-204743, filed Oct. 3, 2014, No. 2015-037507, filed Feb. 27, 2015, and No. 2015-066612, filed Mar. 27, 2015 are hereby incorporated by reference in their entireties in the present application.

The present invention will become more fully understood from the detailed description given below. However, the detailed description and the specific embodiments are only illustrations of the desired embodiments of the present invention, and so are given only for an explanation. Various possible changes and modifications will be apparent to those of ordinary skill in the art on the basis of the detailed description.

The applicant has no intention to dedicate to the public any disclosed embodiment. Among the disclosed changes and modifications, those which may not literally fall within the scope of the present claims constitute, therefore, a part of the present invention in the sense of the doctrine of equivalents.

The use of the articles "a," "an," and "the" and similar referents in the specification and claims are to be construed to cover both the singular and the plural form of a noun, unless otherwise indicated herein or clearly contradicted by the context. The use of any and all examples, or exemplary language (e.g., "such as") provided herein is intended merely to better illuminate the invention, and so does not limit the scope of the invention, unless otherwise stated.

BRIEF DESCRIPTION OF THE DRAWINGS

FIG. 7 is a schematic view of a culture pond of an algae water concentration system according to the present invention, and shows an example in which the culture pond has a light-shielding roof provided thereon.

FIG. 8 is a schematic view of the culture pond and an algae water storage unit of the algae water concentration system according to the present invention.

MODE FOR CARRYING OUT THE INVENTION

Figure 1:
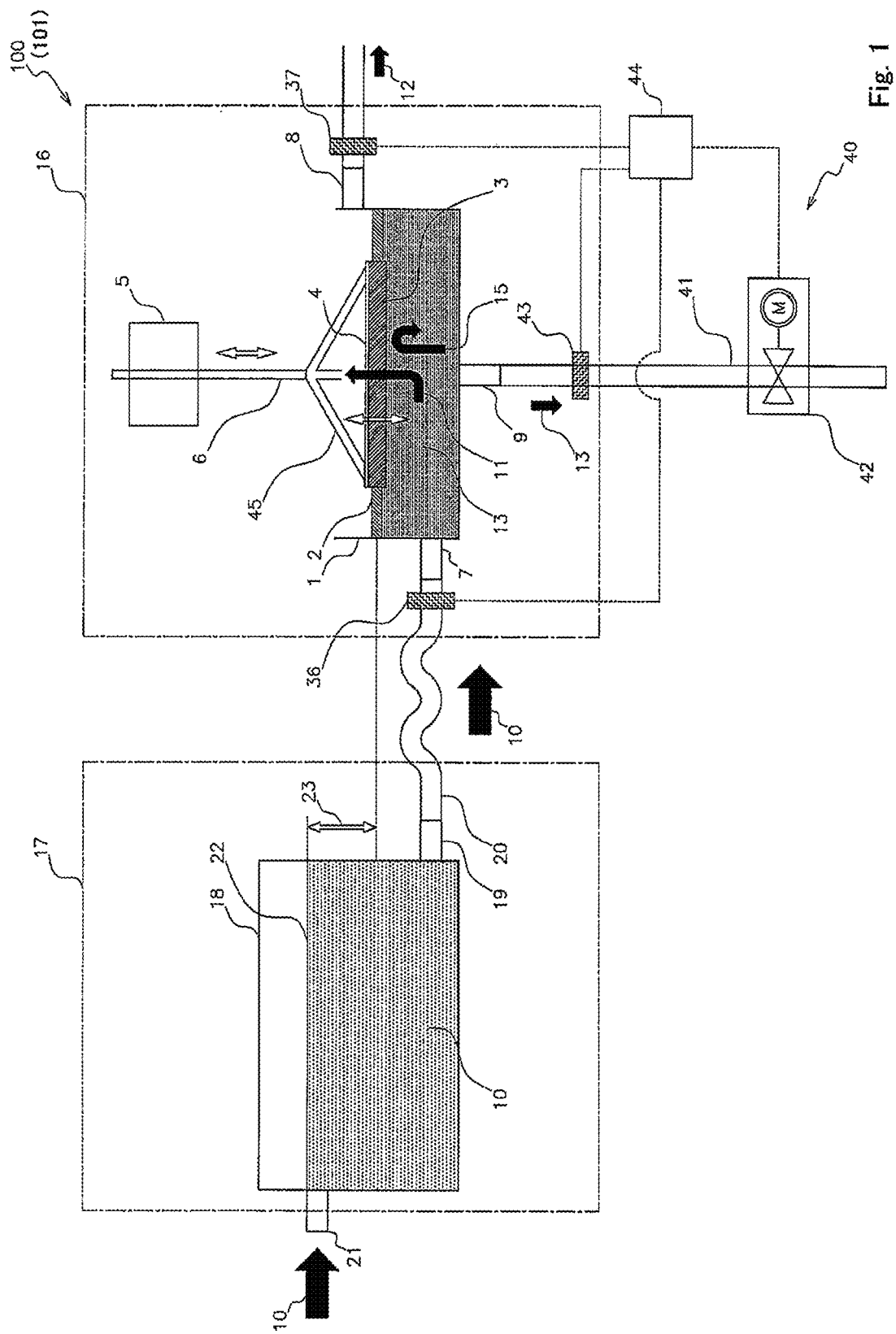
FIG. 1 is a schematic view of a configuration of an algae water concentration unit and an algae water supply unit in an embodiment of an algae water concentration system according to the present invention.

Embodiments of the present invention will be described below with reference to the drawings. In each of the drawings, the same reference numerals will be put on identical or corresponding devices to each other, and duplicated descriptions will be omitted.

Firstly, an algae water concentration system 100 according to a first embodiment of the present invention will be described with reference to FIG. 1. FIG. 1 is a schematic view showing configurations of an algae water concentration unit 16 and an algae water supply unit 17.

The algae water concentration system 100 comprises: an algae water supply unit 17 that receives algae water 10 containing cultured algae from a culture pond (not shown) that cultures algae; and an algae water concentration unit 16 that concentrates the algae water 10 supplied from the algae water supply unit, supplies concentrated algae water 13 to a step on the downstream side, and also discharges filtered water 12 containing algae that are smaller than a predetermined size and water. Furthermore, the algae water concentration system 100 further comprises a concentrated algae water flow rate adjustment apparatus 40 that adjusts the flow rate of the concentrated algae water 13 flowing out from the algae water concentration unit 16.

The algae water supply unit 17 comprises: an algae water supply container 18 that stores the algae water 10 therein; a supply container inlet port 21 through which the algae water supply container 18 takes in the algae water 10 from the culture pond; and a supply container outlet port 19 through which the algae water 10 is taken out from the algae water supply container 18 to the algae water concentration unit 16.

The algae water supply container 18 is a container which can store the algae water 10 therein, and is open to the atmosphere, and the internal pressure thereof results in being atmospheric pressure. The supply container inlet port 21 may be a nozzle installed on the side wall, the ceiling, or the bottom plate of the algae water supply container 18. A tube 26 (see FIG. 2) for conveying the algae water 10 from the culture pond is connected to the supply container inlet port 21. Incidentally, the term "tube" may mean a pipe or a hose. The supply container outlet port 19 is a nozzle fixed to the side wall or the bottom plate of the algae water supply container 18, and is installed below the lowest liquid level of the algae water 10 in the algae water supply container 18 at the time when the system is operating. Incidentally, in order to extract all of the algae water 10 from the algae water supply container 18 for maintenance or the like, the supply container outlet port 19 may be provided at the lowest position of the algae water supply container 18, or a drain nozzle may be additionally provided. A tube 20 for conveying the algae water 10 to the algae water concentration unit 16 is connected to the supply container outlet port 19.

Figure 2:
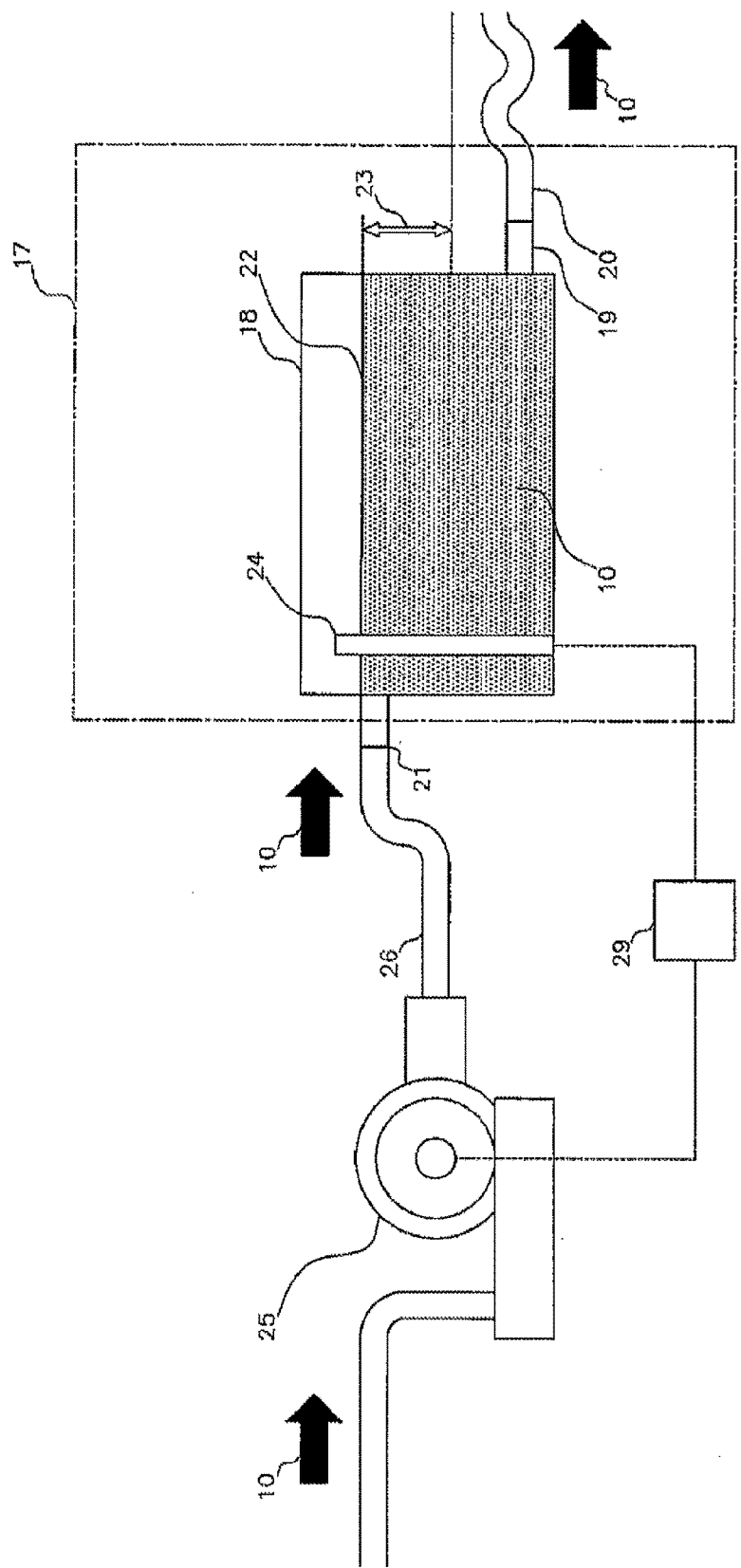
FIG. 2 is a schematic view of an embodiment of a flow rate adjustment device which adjusts a flow rate of algae water to be sent from a culture pond to an algae water supply container.

As is shown in FIG. 2, a liquid level meter 24 that measures the liquid level of the stored algae water 10 is provided to the algae water supply container 18. In addition, a pump 25 is arranged at the tube 26 for conveying the algae water 10 to the algae water supply container 18 from the culture pond. The algae water 10 is pumped from the culture pond to the algae water supply container 18 by the pump 25. Then, the water level control device 29 adjusts the rotation number of the pump 25, based on the liquid level measured by the liquid level meter 24, and controls the amount of the algae water 10 to be conveyed. The water level control device 29 and the pump 25 constitute the algae water flow rate adjustment device. However, the configuration of the algae water flow rate adjustment device is not limited to the above described configuration. When the culture pond is located higher than the algae water supply container 18 and the algae water flows with a gravity flow, a flow control valve may be provided in the tube 26, and the flow rate may be adjusted by the flow rate control valve. The flow rate may be adjusted by other means.

The algae water concentration unit 16 comprises: a concentration container 1 for receiving and concentrating the algae water 10; a filter 3 that divides the concentration container 1 into upper and lower spaces, and does not pass the algae having a predetermined size or larger; a vibration device 5 that vibrates the filter 3 in an out-of-plane direction; a concentration container algae water inlet port 7 that is in communication with the supply container outlet port 19 and takes in the algae water 10 to the concentration container 1 therethrough, and is arranged below the filter 3 of the concentration container 1; a concentrated algae water outlet port 9 that is arranged below the filter 3 of the concentration container 1, and takes out the algae water 13 therethrough that has been concentrated in the concentration container 1; and a filtered water discharge port 8 that is arranged above the filter 3 of the concentration container 1 and discharges filtered water 12 having passed through the filter 3.

The concentration container 1 is a container which can store the algae water 10 therein, and is open to the atmosphere, and the internal pressure thereof results in being atmospheric pressure. The concentration container 1 is typically a cylindrical container, but may have other shapes. A filter 3 is arranged in the inside of the concentration container 1, which divides the inner space into upper and lower spaces (in the case where the upper portion is open, the above-mentioned space is a space on the assumption that the upper portion is closed).

The filter 3 has openings which do not pass algae having a predetermined size or larger therethrough, and passes algae that are smaller than the predetermined size, water, and a substance that is smaller than the predetermined size, therethrough. Here, the predetermined size varies depending on the type of algae to be cultured, but is usually approximately 1 μm to 50 μm. For instance, an electroformed sheet filter or a mesh may be used as the filter 3. Among the materials, an electroformed sheet filter made from the metal is preferable, which filter is not corroded by the algae water 10. The electroformed sheet filter is prevented from being entangled by the algae, as compared to the mesh. In addition, when the electroformed sheet filter is made from metal, the filter is prevented from being entangled by the algae, as compared to a fiber. Furthermore, as will be described later, even when the filter 3 has been vibrated, the electroformed sheet filter is not plastically deformed, which is preferable.

Specific examples of the filter 3 include the following materials.

Figure 3:
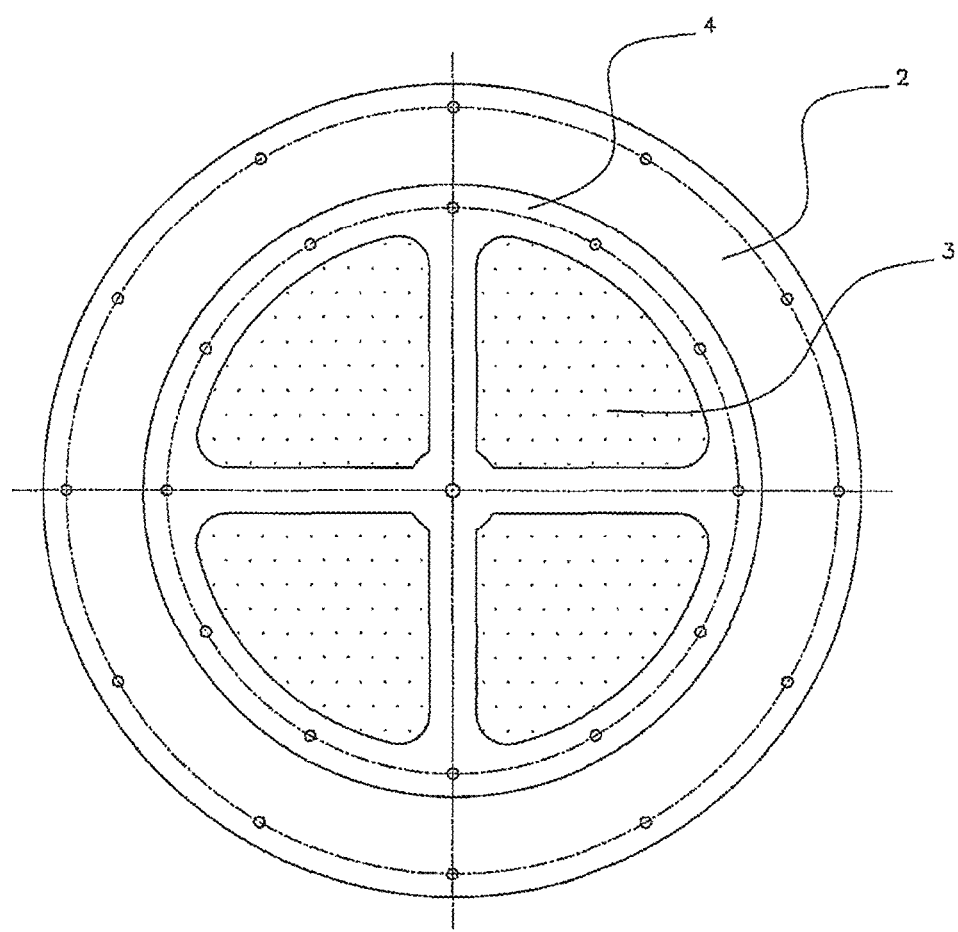
FIG. 3 is a plan view for illustrating the configuration of a filter.
Figure 4:
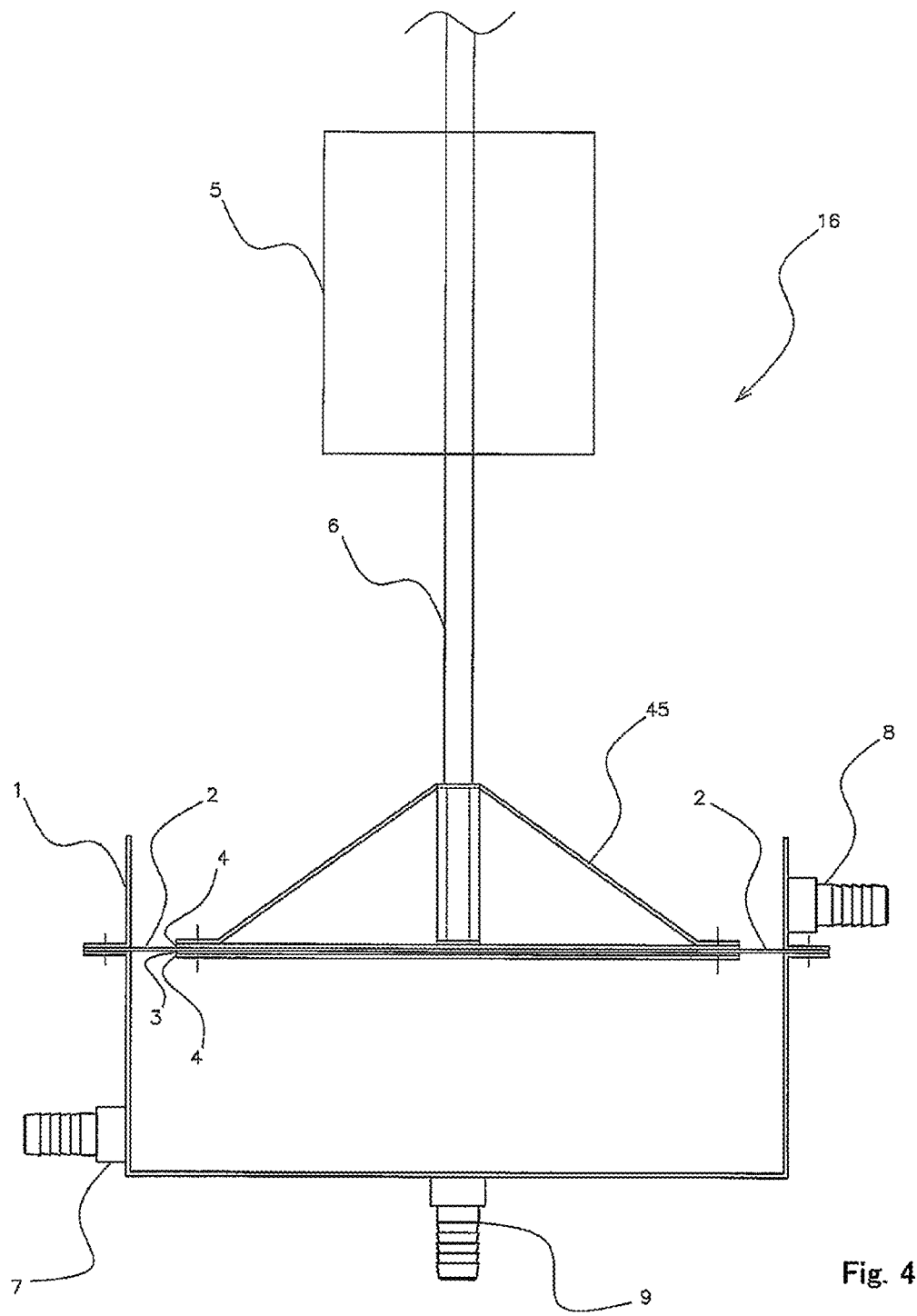
FIG. 4 is a vertical cross-sectional view for illustrating a configuration of the algae water concentration unit.

Metal mesh
Material: stainless steel or the like
Diameter of opening: 30 to 50 μm
Manufacturing method: weaving fine wire
Electroformed mesh
Material: nickel, nickel alloy or the like
Diameter of opening: 1 to 50 μm
Manufacturing method: Patterning of mesh by lithography (ultraviolet rays, X rays or the like) and electroforming is shown in FIG. 3 and FIG. 4, the filter 3 is sandwiched and held between the two filter frames 4 from upper and lower parts, together with a flexible sealing material 2. The flexible sealing material 2 is an annular plate which is formed of, for instance, a stainless steel sheet. The outer periphery of the flexible sealing material 2 is fixed to the concentration container 1, as is shown in FIG. 4. Incidentally, FIG. 3 is a plan view for describing a configuration of the filter 3; and FIG. 4 is a vertical cross-sectional view showing a concentration container 1, a concentration container algae water inlet port 7, a filtered water discharge port 8, a concentrated algae water outlet port 9, a filter 3, a flexible sealing material 2, a filter frame 4, a vibration device 5, a connection mechanism 6, and a filter driving arm 45, in the algae water concentration unit 16. In addition, the flexible sealing material is configured so that the algae water 10 does not pass between the concentration container 1 and the flexible sealing material 2. The filter frame 4 is formed of, for instance, a stainless steel sheet, and is an annular plate that has substantially the same outer shape as that of the filter 3. Furthermore, in order to suppress excessive deformation that occurs while the filter 3 is vibrating, the filter frame 4 preferably has a reinforcing plate which connects the inner periphery of the annular ring of the filter frame 4 in a cross shape. When the filter frame is thus configured, the filter 3 is prevented from being damaged by such a force that the algae water 10 pushes it up. When the filter 3 is fixed to the concentration container 1 through the flexible sealing material 2, the filter 3 tends to be easily vibrated in the out-of-plane direction, because the flexible sealing material 2 is deformed. In addition, since the filter 3 is sandwiched and held between the two filter frames 4, it is easy to exchange the filter 3. Therefore, by exchanging the filter 3 in the same algae water concentration system 100, it becomes easy to concentrate the algae water containing algae having various sizes.

Incidentally, the configuration for holding the filter 3 is not limited to the above described configuration. The configuration may be such a configuration that the algae water 10 does not pass between the filter 3 and the concentration container 1, and also that the filter 3 can be vibrated in the out-of-plane direction. For instance, the periphery of the filter 3 may be fixed with a circular ring which slides on the inner surface of the concentration container 1. In addition, the shape of the filter 3 is not limited to the circular shape, and may be a polygonal shape or another shape.

A vibration device 5 for vibrating the filter 3 in the out-of-plane direction is provided above the concentration container 1. The position of the vibration device 5 is not limited to the upper part of the concentration container 1, but the upper part of the concentration container 1 is preferable, because the vibration device 5 is not exposed to a splash of the algae water 10 or the filtered water 12, and is easily maintained. The position is particularly preferable when the upper part of the concentration container 1 is opened. An operation of vibrating the filter 3 in the out-of-plane direction means that a vertical component is included in the vibration of the filter 3 which is almost horizontally arranged, and includes the case where the filter 3 vibrates in a diagonal direction including a horizontal component. The vibration device 5 is typically an electromagnetic vibration generator, but may be other vibration generators. When an electromagnetic vibration generator is used as the vibration device 5, it is preferable for the vibration device to generate electromagnetic vibration at a voltage (100 V or 200 V) and a frequency (50 Hz to 60 Hz) of a commercial power source. This is because the filter 3 can exhibit an effect, which will be described later, by vibration at the frequency of approximately 50 Hz to 60 Hz. Thus the need for an inverter or the like for converting the frequency is eliminated, and the device can be simplified. Furthermore, the frequency of approximately 50 Hz to 60 Hz is comparatively low, the algae are not damaged by the vibration. Incidentally, the amplitude is, for instance, approximately 0.1 to 1 mm.

The vibration, which has been generated by the vibration device 5, is transmitted to the filter 3 through a connection mechanism 6. The connection mechanism 6 is composed of, for instance, a rod that is arranged in the vertical direction and is connected to the output shaft of the vibration device 5, and of a filter driving arm 45 which disperses and transmits the vibration of the rod to the filter frame 4. The filter driving arm 45 includes four arms, of which the upper portions are connected to the rod, and which connect the upper portions thereof to the annular portion of the filter frame 4. Furthermore, the lower portion of the rod is connected to the center of the cross-shaped reinforcing plates of the filter frame 4. When the connection mechanism is thus configured, the vibration force is uniformly transmitted to the filter frame 4, and the filter 3 tends to easily uniformly vibrate. Incidentally, the configuration of the connection mechanism 6 is not limited to the above described configuration. The number of arms may be three, or also five or more. In addition, the connection mechanism 6 may have another known configuration which can transmit the vibration generated by the vibration device 5 to the filter 3.

The concentration container algae water inlet port 7 is arranged below the filter 3 of the concentration container 1. The concentration container algae water inlet port 7 is connected with the tube 20, and is in communication with the supply container outlet port 19. Therefore, the concentrated container algae water inlet port 7 can take in the algae water 10 of the algae water supply container 18 to the concentration container 1. A supplied algae water flow meter 36 that measures the flow rate of the algae water flowing from the algae water supply container 18 to the concentration container 1 through the tube 20 is installed on the tube 20 in between the supply container outlet port 19 and the concentration container algae water inlet port 7.

The concentrated algae water outlet port 9 is arranged below the filter 3 of the concentration container 1. As will be described later, the algae water 10, which has been taken into the concentration container 1 from the concentration container algae water inlet port 7, is filtered by the filter 3. The algae water in a space below the filter 3 becomes concentrated algae water 13, in which the algae having a predetermined size or larger is concentrated. Thus the concentrated algae water 13 is taken out from the concentration container 1. A concentrated algae water tube 41 is connected to the concentrated algae water outlet port 9, and conveys the concentrated algae water 13 to the next step.

A concentrated algae water tube 41 is connected to the concentrated algae water outlet port 9. A concentrated algae water flow meter 43 is provided on the concentrated algae water tube 41. The meter 43 measures the flow rate of the concentrated algae water 13 that is conveyed from the algae water concentration system 100 to the next step. A flow rate adjustment valve 42 is provided on the tube. The valve 42 adjusts the flow rate of the concentrated algae water 13 that is conveyed from the algae water concentration system 100 to the next step. A concentrated algae water control device 44 adjusts a degree of opening of the flow rate adjustment valve 42, based on the flow rate measured by the concentrated algae water flow meter 43, and thereby can adjust the amount of the concentrated algae water 13 to be taken out from the concentration container 1. Namely, the concentrated algae water flow rate adjustment apparatus 40 can be configured to have the concentrated algae water flow meter 43, the flow rate adjustment valve 42, and the concentrated algae water control device 44. Incidentally, the configuration of the concentrated algae water flow rate adjustment apparatus 40 is not limited to the above configuration. For instance, the flow rate may be adjusted by changing the height of a place to which the concentrated algae water 13 is conveyed. It may be adjusted by preparing a plurality of paths having different flow path resistances, selecting an appropriate path, and making the concentrated algae water flow through the path. Alternatively, any other known flow rate adjustment means can be used.

The filtered water discharge port 8 is arranged above the filter 3 of the concentration container 1, and discharges the filtered water 12 having passed through the filter 3 from the concentration container 1. However, if the filtered water discharge port 8 were arranged at a position excessively higher than that of the filter 3, the weight of the filtered water 12 on the filter 3 would increase to make it difficult for the vibration device 5 to vibrate the filter 3 in the out-of-plane direction. Thus, the filtered water discharge port 8 is arranged at a position which is, for instance, 1 to 5 mm higher than that of the filter 3, and preferably is 1 to 2 mm higher than that of the filter 3. Typically, a tube is connected to the filtered water discharge port 8, and the filtered water 12 is returned to a culture pond (not-shown) therethrough. The filtered water 12 may be used for another purpose, or may be discarded. It is preferable that the filtered water discharge port 8 is configured to allow the filtered water 12 to flow at a higher flow rate than a necessary flow rate so that the liquid level of the filtered water 12 having passed through the filter 3 coincides with the height of the filtered water discharge port 8. The system has a filtered water drainage flow meter 37 that measures the flow rate of the filtered water 12 flowing out from the filtered water discharge port 8 to transmit the flow rate of the filtered water 12 to the concentrated algae water control device 44. Therefore, the concentrated algae water control device 44 can calculate the total flow rates of the concentrated algae water 13 and the filtered water 12, both flowing out from the concentration container 1.

Next, the operation of the algae water concentration system 100 will be described. Firstly, the algae water supply container 18 takes in the algae water 10 from a culture pond. Then, the concentration container 1 takes in the algae water 10 from the algae water supply container 18. In the concentration container 1, the algae water is taken in until the filter 3 is immersed in the algae water 10. Incidentally, when the algae water concentration system 100 is operated and then stopped, if the filter 3 is positioned higher than the liquid level of the filtered water 12, the filter 3 is exposed to air. Then, a surface tension is generated in the algae water 10 remaining in the opening of the filter 3. For this reason, the algae water 10 remaining in the opening obstructs the opening so that the air cannot escape from a space between the filter 3 and the concentrated algae water 13 or the algae water 10 below the filter 3. Thus the concentrated algae water 13 or the algae water 10 cannot contact with the filter 3. Because of this, the concentration operation of the algae water cannot be restarted. Specifically, it is preferable that the filter 3 is always immersed in the algae water 10 or the filtered water 12. Thus, the filtered water discharge port 8 is arranged at a position higher than the highest position of the vibrating filter 3.

In a state in which the filter 3 is immersed in the algae water 10 or the filtered water 12, the vibration device 5 is activated to vibrate the filter 3. When the filter 3 vibrates, the filter 3 thereby can prevent the algae from adhering to it. But when the vibration is stopped, the algae adhere to the filter and result in obstructing the opening. The operation up to the above is an operation preparation stage.

In order to start the operation, it is preferable to set the liquid level 22 of the algae water 10 in the algae water supply container 18 to a position that is higher than the height of the filter 3 by a predetermined level difference 23. Since the height of the filter 3 is practically determined, the liquid level 22 of the algae water 10 in the algae water supply container 18 may be adjusted, as has been described with reference to FIG. 2. When the water level difference 23 is excessively large, the force with which the algae water 10 pushes up the filter 3 (including the filter frame 4 and the like) increases. Then, the force is transmitted from the connection mechanism 6 to the vibration device 5, a large driving force is needed to vibrate the vibration device 5. In some cases, the vibration device 5 is not operated. On the contrary, if the water level difference 23 is excessively small or if the liquid level 22 of the algae water 10 in the algae water supply container 18 is lower than the height of the filter 3, the algae water 10 sent from the algae water supply container 18 does not pass through the filter 3. Therefore, the algae water 10 is not concentrated in the concentration container 1. Thus, the predetermined water level difference 23 is generally set at approximately 100 mm to 300 mm, though it varies depending on the conditions such as the type of algae and the size of the opening of the filter 3.

When the water level difference 23 is kept to a predetermined value, the algae water 10 flows out from the algae water supply container 18 through the tube 20. It is taken into the concentration container 1 through the concentration container algae water inlet port 7. The flow rate of it is measured by the supplied algae water flow meter 36. The measured flow rate of the algae water 10 that is taken into the concentration container 1 is transmitted to the concentrated algae water control device 44.

A part of the algae water 10 that has been taken into the concentration container 1 reaches the filter 3. Small algae having a smaller size than that of the opening of the filter 3, other floating substances, and the water 11 out of the algae water 10, pass through the opening and flow toward the upper part of the filter 3 as the filtered water 12. The filtered water 12 that has flowed to the upper part of the filter 3 is discharged to the outside of the concentration container 1 through the filtered water discharge port 8. The flow rate is measured by the filtered water drainage flow meter 37 to be transmitted to the concentrated algae water control device 44.

Algae 15 having a larger size than that of the opening of the filter 3 in the algae water 10, which has reached the filter 3, cannot pass through the opening to stay in the space below the filter 3. At this time, even though the algae have reached the filter 3, since the filter 3 is vibrated in the out-of-plane direction, the algae are reflected by the filter 3 to be prevented from adhering to the filter 3. Thus the opening is prevented from being clogged. Namely, the cleaning of the filter 3 is unnecessary.

Thus, the algae having a smaller size than that of the opening of the filter 3, other floating substances, and the water 11 pass through the opening toward the upper part of the filter 3, as the filtered water 12, and the algae 15 having a larger size than that of the opening stay in the space below the filter 3. Accordingly, concentrated algae water 13, in which the algae having a predetermined size or larger are concentrated, is produced in the space under the filter 3. The concentrated algae water 13 in the space below the filter 3 is taken out through the concentrated algae water outlet port 9 while the flow rate is adjusted by the concentrated algae water flow rate adjustment apparatus 40. It is sent to the next step, for instance, a drying step and an oil extraction step. Incidentally, the flow rate of the concentrated algae water 13 that flows out through the concentrated algae water outlet port 9 is measured by the concentrated algae water flow meter 43 to be transmitted to the concentrated algae water control device 44.

The concentrated algae water control device 44 receives the flow rate of the algae water 10 that is taken into the concentration container 1, which has been measured by the supplied algae water flow meter 36, the flow rate of the filtered water 12 that is discharged from the concentration container 1 to the outside of the concentration container 1, which has been measured by the filtered water drainage flow meter 37, and the flow rate of the concentrated algae water 13 that flows out from the concentration container 1, which is measured by the concentrated algae water flow meter 43. Then, the concentrated algae water control device 44 can calculate a concentration rate in the concentration container 1, based on the flow rate of the algae water 10 that enters into the concentration container 1, the flow rate of the filtered water 12 that is discharged from the concentration container 1, and the flow rate of the concentrated algae water 13 that flows out from the concentration container 1. In other words, the concentrated algae water flow rate adjustment apparatus 40 can adjust the flow rate of the concentrated algae water 13 flowing out from the concentration container 1 so that the concentrated algae water 13 has a desired concentration. The algae water concentration system 100 is enabled to obtain the concentrated algae water 13 having a desired concentration by a continuous operation. Furthermore, the algae water concentration system 100 can check whether or not leakage has occurred therein, based on the flow rate of the algae water 10 that flows into the concentration container 1, and the flow rates of the filtered water 12 and the concentrated algae water 13 that flow out from the concentration container 1.

The concentrated algae water 13 in the space below the filter 3 of the concentration container 1 is stirred by the flow of the algae water 10 that flows in through the concentration container algae water inlet port 7 so that the degree of the concentration becomes uniform. However, the degree of the concentration occasionally becomes non-uniform, due to the capacity of the concentration container 1, the flow rate of the flowing algae water 10, the flow speed, the size of the algae, or the like. In this case, a stirring device (not-shown) may be installed in the space below the filter 3 of the concentration container 1.

In the above description, it has been described that the concentrated algae water control device 44 receives the flow rate of the algae water 10 that is taken into the concentration container 1, which has been measured by the supplied algae water flow meter 36, the flow rate of the filtered water 12 that is discharged from the concentration container 1 to the outside of the concentration container 1, which has been measured by the filtered water drainage flow meter 37, and the flow rate of the concentrated algae water 13 that flows out from the concentration container 1, which is measured by the concentrated algae water flow meter 43, and that the water level control device 29 receives the liquid level of the algae water supply container 18, which has been measured by the liquid level meter 24. However, it is also acceptable that one control device receives all these measured values, adjusts the water level difference 23, and adjusts the concentration rate.

In the above description, it has been described that both of the flow rates are measured, i.e., the flow rate of the filtered water 12 that is discharged from the concentration container 1 to the outside of the concentration container 1, which has been measured by the filtered water drainage flow meter 37, and the flow rate of the concentrated algae water 13 that flows out from the concentration container 1, which is measured by the concentrated algae water flow meter 43. However, only one of the flow rates may be measured to adjust the concentration rate.

EXAMPLE

A concentration test for the algae water was carried out with the use of the following device.
(Test Device)
Filter: electroformed sheet having diameter of opening of 30 μm
Filter area: 150 cm²
Vibration device: Electromagnetic vibration generator, AC 100 V, 50 Hz
Water level difference between liquid level of algae water supply container and filter: 150 mm
Vibration of filter: vertical direction, amplitude of 0.5 mm, and frequency of 50 Hz
(Test Result)
Filtration speed: (during vibration) 28 cc/cm²/min
(Vibration halt) Filtered water stops flowing in approximately 1 minute after vibration has stopped.
In the above test, it was confirmed that when the filter was vibrated in the out-of-plane direction, the filtered water passed through the filter surface, and when the vibration of the filter stopped, the passage of the filtered water also stopped. When the filtered water was observed under a microscope, algae with 30 μm or larger were not almost observed. It is considered that due to the vibration of the filter, algae having a larger size than that of the opening of the filter were bounced back and did not adhere to the opening of the filter, and algae having a smaller size than that of the opening of the filter and the water passed through the opening of the filter. It is considered that when the vibration was stopped, the algae adhered to the opening and closed the opening so that the filtered water did not pass through the filter.

Figure 5:
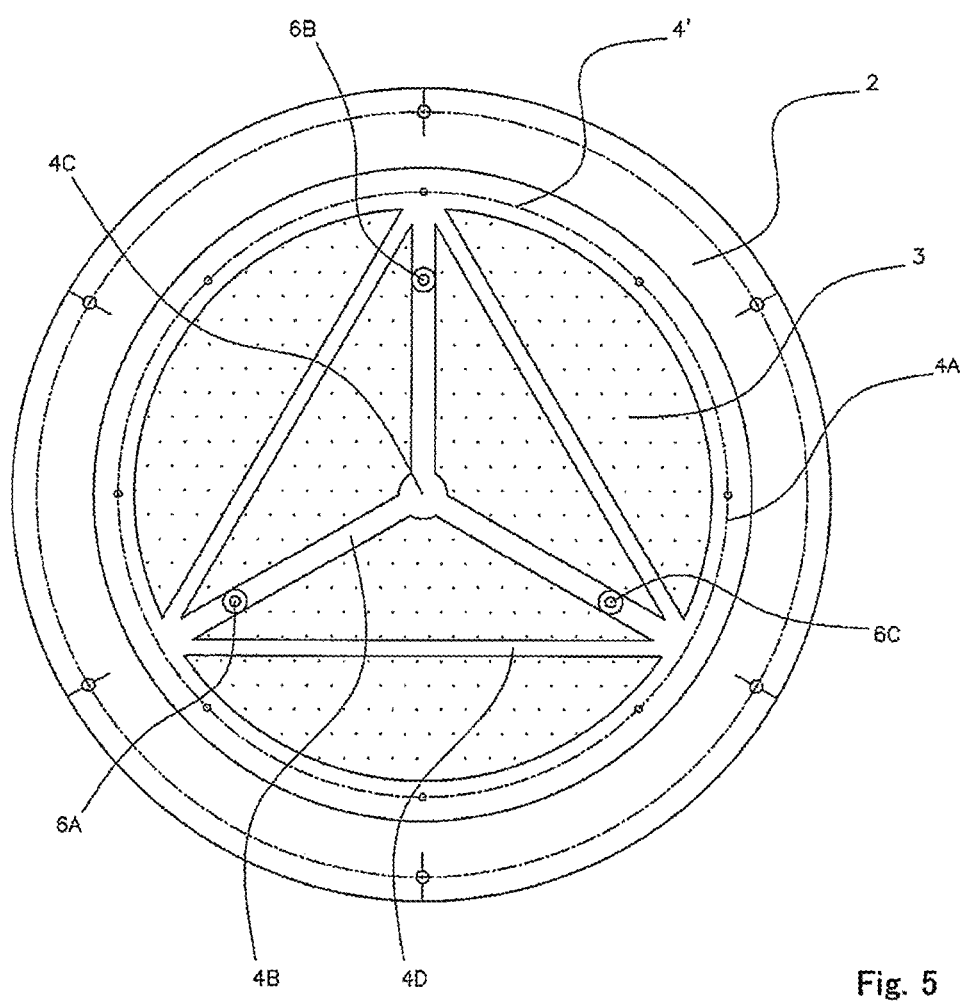
FIG. 5 is a plan view for illustrating a configuration of a filter that is different from that in FIG. 3.
Figure 6:
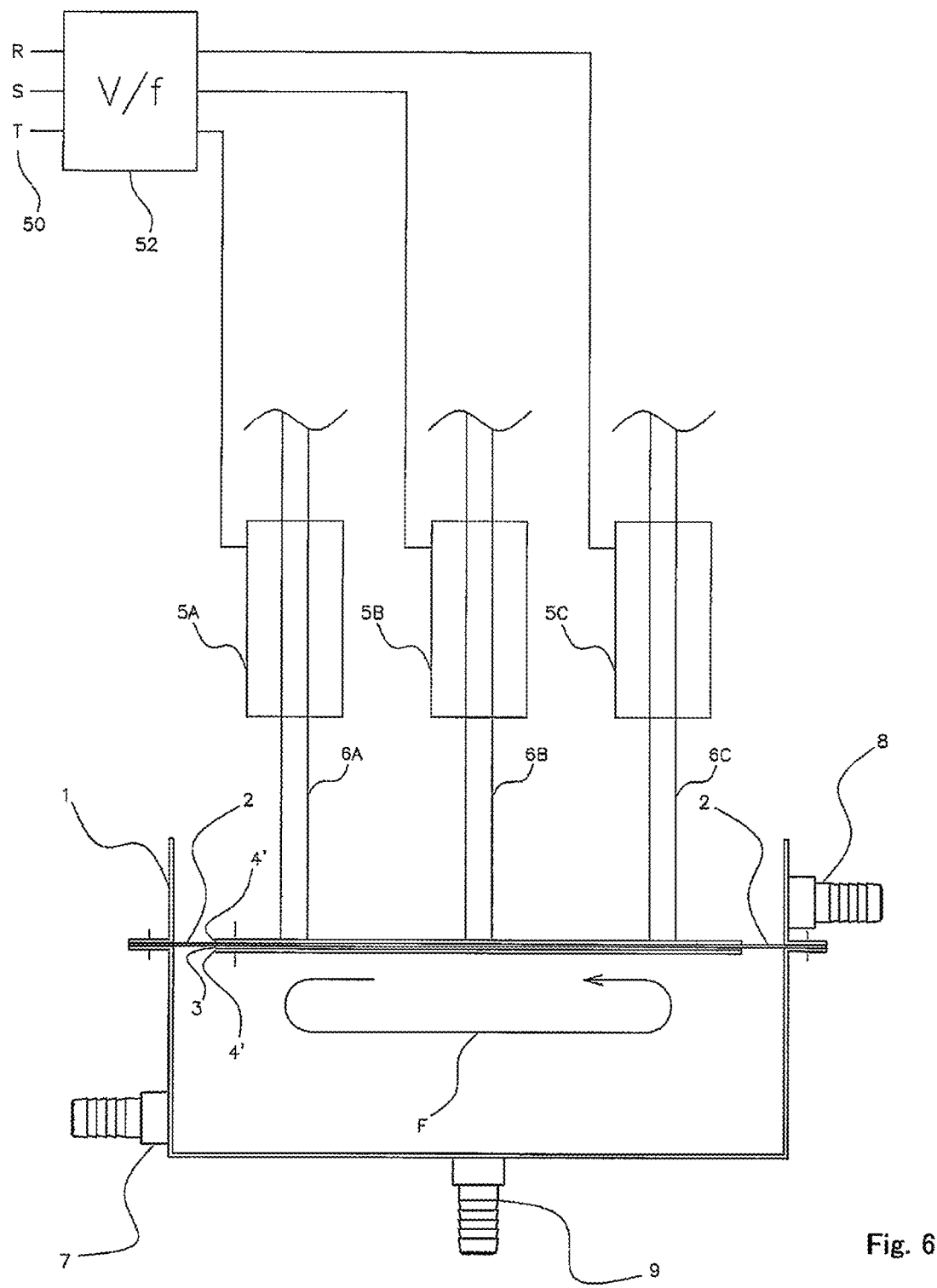
FIG. 6 is a conceptual view for illustrating a vibration device of the filter shown in FIG. 5.

Next, another example of the filter 3 and the vibration device 5 will be described with reference to FIG. 5 and FIG. 6. FIG. 5 is a plan view for describing the filter 3 in another example; and FIG. 6 is a conceptual view for describing the filter 3 and the vibration devices 5A, 5B and 5C. The filter 3 itself is the same as that shown in FIG. 3. However, the filter frame 4' is different from the filter frame 4 in a point that the filter frame 4' has three reinforcing plates 4B which connect the annular outer frame 4A with the center 4C. The reinforcing plates 4C are arranged at equal central angles, namely, at spacing of 120°. Incidentally, in the case where the equal central angles are described, the equal central angles need not to be strictly equal spacing, and the angles may have the spacing in such a degree as to generate a flow in a parallel direction to the filter 3 in the concentrated algae water 13 below the filter 3, which will be described later. In addition, the three vibration devices 5A, 5B and 5C are connected to the reinforcing plates 4B, through the connection mechanisms 6A, 6B and 6C, respectively.

The positions at which the connection mechanisms 6A, 6B and 6C are connected to the reinforcing plates 4B, respectively, are not necessarily limited, but the connection mechanisms 6A, 6B and 6C are preferably arranged on the circumference of a circle. The position may be an intersection of the reinforcing plate 4B and the annular outer frame 4A (i.e., within annular outer frame 4A). When being connected to the annular outer frame 4A or a portion close thereto, the vibration device can vibrate the filter 3 with a small force. When being connected to a position close to the center 4C, the vibration device can vibrate the whole filter 3 even with small vibration.

Incidentally, in the example shown in FIG. 5, the connection mechanisms 6A, 6B and 6C are connected to portions on the reinforcing plates 4B, respectively, which are close to the annular outer frame 4A. When the connection mechanisms 6A, 6B and 6C are connected to the portions on the reinforcing plates 4B, respectively, which are close to the annular outer frame 4A, large distortion may be generated in connection portions between the reinforcing plates 4B and the outer frame 4A, by the vibration which is applied to the reinforcing plates 4B through the connection mechanisms 6A, 6B and 6C. Thus three second reinforcing plates 4D are further provided to the respective intersections of the annular outer frame 4A and the reinforcing plates 4B. However, the second reinforcing plates 4D are not indispensable.

The vibration devices 5A, 5B and 5C receive the R phase, the S phase and the T phase from a power source 50 of the three-phase alternating current. For this reason, electric currents each having a phase difference of 120° to each other are supplied to the vibration devices 5A, 5B and 5C. Therefore, the vibrations of the vibration devices 5A, 5B and 5C have the phase difference of 120° to each other. Therefore, the filter frame 4' and the filter 3 vibrate so as to wave in the circumferential direction.

Because the filter frame 4' and the filter 3 vibrate so as to wave, a flow F in a parallel direction to the filter 3 is formed in the concentrated algae water 13, below the undersurface of the filter 3. As a result, the algae below the undersurface of the filter 3 are prevented from adhering to the filter, by means of the flow F in the parallel direction. Specifically, the algae are further prevented from adhering to the filter by the flow F in the parallel direction, in addition to the vertical vibration.

It is preferable that the vibration devices 5A, 5B, and 5C have a frequency converter (so-called three-phase inverter) 52 which converts the frequency of the electric current flowing from the power source 50 to the vibration devices 5A, 5B and 5C to change vibration speeds of the vibration devices 5A, 5B, and 5C. Since the vibration speeds of the vibration devices 5A, 5B, and 5C are changed, the flow speed of the flow F in the parallel direction to the filter 3 is changed. Further, the strength of the flow F can be changed, and a function of preventing the adhesion of the algae can be enhanced.

In the above description, it has been described that the number of the reinforcing plates 4C has been set at three, and also the numbers of the vibration devices 5A, 5B 5C and the connection mechanisms 6A, 6B and 6C have been set at three, but the numbers may be multiples of three. If the area of the filter 3 increases, for instance, the number of the reinforcing plates 4C may be six, and also the numbers of the vibration devices 5 and the connection mechanisms 6 may be each six; and may also be nine plates and nine devices and mechanisms. As long as the number is the multiple of 3, the vibration devices can give vibrations having a phase difference to each other to the filter 3, by using the three-phase alternating current.

In addition, in order to prevent the filter frame 4' and the filter 3 from being bent in the vicinity of the center 4C, a filter support mechanism (not-shown) may be provided, which is connected to the center 4C. In the case where the vertical vibration of the filter 3 in the vicinity of the center 4C becomes small due to the structure of the filter 3, and where there is a possibility that the algae adhere to the filter 3, a vibration device may be provided on the filter support mechanism, and vibrate the center 4C. In this case, that vibration device may have a different vibration frequency or a phase from the other vibration devices, or may have those equal to those in any of the vibration devices. When the center 4C vibrates vertically, the vibration can prevent the algae from adhering to the filter 3 in the vicinity of the center 4C.

Next, the algae water concentration system 101 according to the second embodiment of the present invention will be described with reference to FIG. 7. The algae water concentration system 101 further has an algae water storage unit that stores the algae water containing the cultured algae therein, and stores the algae water for a predetermined time period, in a state in which light is blocked, in which there is no water flow, and in which nutrients are not given, on the upstream side of the algae water supply unit 17, in addition to the algae water concentration system 100, which has been described. FIG. 7 shows an example in which a light shielding roof 64 is installed above a culture pond 60. The light shielding roof 64 is installed above the culture pond 60, which covers the top face of the culture pond 60 and blocks sunlight. The light shielding roof 64 can be opened and closed; and takes the sunlight into the culture pond 60 when being opened, and blocks the sunlight when being closed. The light shielding roof 64 may be opened and closed by sliding the light shielding roof 64 on a rail (not-shown), which is laid on the culture pond 60, or may also be opened and closed by swinging a plurality of plates about a shaft of one end thereof like a shutter of a camera; and may also be opened and closed by any other known method.

A water flow generator 66 that generates a water flow is installed in the culture pond 60. The water flow generator 66 circulates the water in the culture pond 60 to spread the nutrients evenly, to grow the algae evenly, and to cause the distribution of the grown algae to be uniform.

On the culture pond 60, while the algae are cultured, the light shielding roof 64 is opened, and the sunlight is taken into the culture pond 60. Furthermore, the water flow generator 66 is operated to generate the water flow, and necessary nutrients are given to the algae to culture the algae. When the algae are cultured to a predetermined level, the light shielding roof 64 is closed to block the light, the water flow generator 66 is stopped to turn the culture pond into a state in which there is no water flow, and no nutrients are given to the algae. Namely, the culture pond 60 is used as an algae water storage unit. Then, after a predetermined time period, for instance, three days to one week has passed, the algae water 10 is sent to the algae water supply unit 17 through the tube 68 and the pump 25.

FIG. 8 shows further another example of an apparatus that stores the algae water 10 containing the cultured algae therein for a predetermined time period, in a state in which light is blocked, in which there is no water flow, and in which nutrients are not given. In the example shown in FIG. 8, a pond giving no stress 62, that stores the algae water 10 therein, is provided in the tube 68 that leads to the algae water supply unit 17 from the culture pond 60. The pond giving no stress 62 stores the algae water 10 for a predetermined time period, in a state in which light is blocked, in which there is no water flow, and in which nutrients are not given. Namely, the pond giving no stress 62 is an algae water storage unit. A light shielding roof 64 is installed on the pond giving no stress 62, which covers the top face of the pond and blocks the sunlight. The structure of the light shielding roof 64 is similar to that described for the culture pond 60. Incidentally, even in the case where the pond giving no stress 62 is provided, the water flow generator 66 is installed in the culture pond 60. Therefore, if the inflow of the algae water 10 from the culture pond 60 and the outflow of the algae water to the algae water supply unit 17 have stopped, the pond giving no stress becomes a state of having no water flow. The algae water 10 may be sent from the culture pond 60 to the pond giving no stress 62 by a not-shown pump or may be sent by the height difference. When the algae water 10 is sent by the height difference, a valve or a water gate (not shown) is installed which stops the flow of the algae water 10. Incidentally, the tube 68 that leads to the algae water supply unit 17 from the culture pond 60 may be a groove in which the algae water 10 flows.

In place of the pond giving no stress 62, a container may be installed as the algae water storage unit. A lid or roof of the container may be configured to be an opening and closing type. The shape of the container has an arbitrary shape. When the container is used as the algae water storage unit, it becomes easy to store the algae water in a state in which light is blocked, in which there is no water flow, and in which nutrients are not given. Further, it becomes easy to install the light shielding roof 64 or the lid. On the other hand, in the case of the pond giving no stress 62, it is possible to inexpensively prepare a large algae water storage unit.

Next, a method for operating the algae water concentration system 101, specifically, a method for concentrating the algae water containing the culture algae, will be described. Firstly, algae are cultured in the culture pond 60. When the algae are cultured, it is preferable to expose the algae to sunlight, give nutrients to the algae, and operate the water flow generator 66 to generate the water flow and to circulate the water. When the algae have grown, the algae water 10 is to be concentrated.

Thus, firstly, the algae water 10 is stored for a predetermined time period in a state in which light is blocked, in which there is no water flow, and in which nutrients are not given. As is shown in FIG. 7, the light shielding roof 64 of the culture pond 60 is closed to block light, the water flow generator 66 is stopped to turn the culture pond 60 to the state in which there is no water flow, and no nutrients are given to the algae. Alternatively, as is shown in FIG. 8, the algae water 10 is stored in the pond giving no stress 62, the light shielding roof 64 is closed to block light, and no nutrients are given to the algae, in a state in which there is no water flow. The algae water 10 may not be stored in the pond giving no stress 62, but in the container. It is preferable that the predetermined time period is set at three days to one month or shorter. If the algae water 10 has been stored for 3 days, the mucus almost disappears. In order to eliminate the mucus more, it is preferable to store the algae water for approximately 5 days, and is more preferable to store the algae water for one week. When the storage period becomes excessively long, the operation status of the facility deteriorates, which is not economically preferable. For this reason, the storage period is preferably as short, for instance, as 2 weeks or shorter, or 1 week or shorter, and further 5 days or shorter.

When having been stored for the predetermined time period in a state in which light is blocked, in which there is no water flow, and in which nutrients are not given, the algae water 10 is taken into the algae water supply container 18. The algae water 10 may be taken into the algae water supply container 18, by a not-shown pump or by a height difference.

The operation after the algae water 10 has been taken into the algae water supply container 18 is similar to the operation of the algae water concentration system 100, and accordingly duplicated description will be omitted. Incidentally, since the algae water 10 is stored for the predetermined time period in a state in which light is blocked, in which there is no water flow, and in which nutrients are not given, the mucus of the algae disappears so that the clogging of the filter 3 by the mucus does not occur. Accordingly, no opening is clogged. Namely, the cleaning of the filter 3 is unnecessary. Therefore, even in the case where the algae tend to easily secrete the mucus, the algae water can be suitably concentrated.

Reference numerals used in the present specification will be collectively shown below.
- 1: Concentration container
- 2: Flexible sealing material
- 3: Filter
- 4 and 4': Filter frame
- 4A: Annular outer frame
- 4B: Reinforcing plate
- 4C: Center
- 4D: Second reinforcing plate
- 5, 5A, 5B and 5C: Vibration device
- 6, 6A, 6B and 6C: Connection mechanism
- 7: Concentration container algae water inlet port
- 8: Filtered water discharge port
- 9: Concentrated algae water outlet port
- 10: Algae water
- 11: Algae having smaller size than that of opening, other floating substances and water
- 12: Filtered water
- 13: Concentrated algae water
- 15: Algae having larger size than that of opening
- 16: algae water concentration unit
- 17: Algae water supply unit
- 18: Algae water supply container
- 19: Supply container outlet port
- 20: Tube
- 21: Supply container inlet port
- 22: liquid level of algae water in algae water supply container
- 23: water level difference
- 24: Liquid level meter
- 25: Pump
- 26: Tube
- 29: Water level control device
- 36: Supplied algae water flow meter
- 37: Filtered water drainage flow meter
- 40: Concentrated algae water flow rate adjustment apparatus
- 41: Concentrated algae water tube
- 42: Flow rate adjustment valve
- 43: Concentrated algae water flow meter
- 44: Concentrated algae water control device
- 45: Filter driving arm
- 50: Power source
- 52: Frequency converter
- 60: Culture pond
- 62: pond giving no stress (algae water storage unit)
- 64: Light shielding roof
- 66: Water flow generator
- 68: Tube
- 100 and 101: Algae water concentration system
- F: Flow in parallel direction to filter for algae water

The invention claimed is:

1. A cultured algae water concentration system comprising:
   an algae water supply unit that receives algae water containing cultured algae from a culture pond, stores the algae water therein, and has an algae water supply container that stores the algae water therein,
   a supply container inlet port through which the algae water supply container takes in the algae water, and
   a supply container outlet port through which the algae water is taken out from the algae water supply container; and
   an algae water concentration unit that concentrates the algae water which has been supplied from the algae water supply unit, and that has
   a concentration container for receiving and concentrating the algae water,
   a planar filter that divides the concentration container into upper and lower spaces and does not pass algae having a predetermined size or larger therethrough,
   a vibration device that vibrates the filter in a
   direction that does not lie within a plane of the planar filter when at rest,
   a concentration container algae water inlet port that is in communication with the supply container outlet port, takes in the algae water to the concentration container, and is arranged below the filter of the concentration container,
   a concentrated algae water outlet port that is arranged below the filter of the concentration container and takes out algae water therethrough that has been concentrated in the concentration container, a filtered water discharge port that is arranged above the filter of the concentration container and discharges filtered water having passed through the filter, a liquid level meter that measures a liquid level of the algae water which is stored in the algae water supply container, and an algae water flow rate adjustment device that adjusts a flow rate of the algae water to be sent to the algae water supply container from the culture pond, based on the liquid level, which has been measured by the liquid level meter, wherein the filtered water discharge port is arranged at a position that is higher than the highest position on the filter, which is vibrated by the vibration device wherein the filter is held by a filter frame that has an annular outer frame and reinforcing plates, of which the sheet number of the reinforcing plates is multiples of 3 and which extend from the center to the annular outer frame in a radial direction at equal central angles, the vibration device comprises multiple vibration devices, the reinforcing plates each having a vibration device thereon, wherein the respective vibration device is connected to the corresponding reinforcing plate of the filter frame or intersections between the corresponding reinforcing plate and the annular outer frame, to vibrate the filter through the filter frame.

2. The cultured algae water concentration system according to claim 1, further comprising:

an algae water storage unit that stores the algae water containing cultured algae therein, and stores the algae water for a predetermined time period, in a state in which light is blocked, in which there is no water flow, and in which nutrients are not given, provided on the upstream side of the algae water supply unit.

3. A cultured algae water concentration system comprising:

an algae water storage unit that stores algae water containing cultured algae therein, and stores the algae water for a predetermined time period, in a state in which light is blocked, in which there is no water flow, and in which nutrients are not given; and an algae water concentration unit that concentrates the algae water which has been supplied from the algae water storage unit, and that has a concentration container for receiving and concentrating the algae water, a planar filter that divides the concentration container into upper and lower spaces and does not pass algae having a predetermined size or larger therethrough, a vibration device that vibrates the filter in a direction that does not lie within a plane of the planar filter when at rest, an algae water inlet port that takes the algae water into the concentration container therethrough which algae water has been stored in the algae water storage unit, which algae water inlet port is arranged below the filter of the concentration container, a concentrated algae water outlet port that is arranged below the filter of the concentration container and takes out algae water therethrough that has been concentrated in the concentration container, a filtered water discharge port that is arranged above the filter of the concentration container and discharges filtered water having passed through the filter, a liquid level meter that measures a liquid level of the algae water which is stored in the algae water supply container, and an algae water flow rate adjustment device that adjusts a flow rate of the algae water to be sent to the algae water supply container from the culture pond, based on the liquid level, which has been measured by the liquid level meter, wherein the filtered water discharge port is arranged at a position that is higher than the highest position on the filter, which is vibrated by the vibration device, wherein the filter is held by a filter frame that has an annular outer frame and reinforcing plates, of which the sheet number of the reinforcing plates is multiples of 3 and which extend from the center to the annular outer frame in a radial direction at equal central angles, the vibration device comprises multiple vibration devices, the reinforcing plates each having a vibration device thereon, wherein the respective vibration device is connected to the corresponding reinforcing plate of the filter frame or intersections between the corresponding reinforcing plate and the annular outer frame, to vibrate the filter through the filter frame.

4. The cultured algae water concentration system according to any one of claim 1 to claim 3, further comprising:

a concentrated algae water flow rate adjustment apparatus that adjusts the amount of concentrated algae water flowing out through the concentrated algae water outlet port.

5. The cultured algae water concentration system according to claim 1, wherein electric currents of an R phase, an S phase and a T phase of a three-phase alternating current are supplied to the respective vibration device in an order of a circumferential direction, and the vibration devices vibrate out of phase.

6. The cultured algae water concentration system according to claim 5, further comprising:

a frequency converter that converts a frequency of the three-phase alternating current.

7. The cultured algae water concentration system according to claim 2 or 3, wherein the algae water storage unit is a container that stores the algae water that is received from a culture pond.

8. The cultured algae water concentration system according to claim 2 or 3, wherein the algae water storage unit is a pond that stores the algae water that is received from a culture pond.

9. A method for operating the cultured algae water concentration system according to any one of claim 1 to claim 3, comprising:

a step of operating the vibration device, and then a step of supplying the algae water from the algae water supply unit to the algae water concentration unit.

* * * * *

UNITED STATES PATENT AND TRADEMARK OFFICE
CERTIFICATE OF CORRECTION

PATENT NO. : 10,508,261 B2
APPLICATION NO. : 15/512667
DATED : December 17, 2019
INVENTOR(S) : Toshiro Kisakibaru et al.

It is certified that error appears in the above-identified patent and that said Letters Patent is hereby corrected as shown below:

In the Drawings

Drawing Sheet 2 of 8, consisting of Fig. 2, should be deleted and replaced with the correct Drawing Sheet 2 of 8, consisting of Fig. 2, as shown on the attached page.

Signed and Sealed this
Eighteenth Day of February, 2020

Andrei Iancu
*Director of the United States Patent and Trademark Office*